(12) United States Patent
Menter

(10) Patent No.: US 11,865,097 B2
(45) Date of Patent: Jan. 9, 2024

(54) CREATINE NUTRITIONAL SUPPLEMENT

(71) Applicant: Dylan Menter, Los Angeles, CA (US)

(72) Inventor: Dylan Menter, Los Angeles, CA (US)

( * ) Notice: Subject to any disclaimer, the term of this patent is extended or adjusted under 35 U.S.C. 154(b) by 0 days.

(21) Appl. No.: 18/127,542

(22) Filed: Mar. 28, 2023

(65) Prior Publication Data
US 2023/0233499 A1    Jul. 27, 2023

Related U.S. Application Data

(63) Continuation-in-part of application No. 17/221,787, filed on Apr. 3, 2021, now Pat. No. 11,642,327.

(60) Provisional application No. 63/069,650, filed on Aug. 24, 2020.

(51) Int. Cl.
| | |
|---|---|
| *A61K 31/205* | (2006.01) |
| *A61K 9/00* | (2006.01) |
| *A61K 47/26* | (2006.01) |
| *A23G 3/42* | (2006.01) |
| *A23L 33/175* | (2016.01) |
| *A23L 33/125* | (2016.01) |
| *A23G 3/44* | (2006.01) |
| *A61K 47/36* | (2006.01) |

(52) U.S. Cl.
CPC .............. *A61K 31/205* (2013.01); *A23G 3/42* (2013.01); *A23G 3/44* (2013.01); *A23L 33/125* (2016.08); *A23L 33/175* (2016.08); *A61K 9/0056* (2013.01); *A61K 47/26* (2013.01); *A61K 47/36* (2013.01)

(58) Field of Classification Search
None
See application file for complete search history.

(56) References Cited

U.S. PATENT DOCUMENTS

2010/0226904 A1 *   9/2010   Davis ..................... A23G 3/48
                                                                    424/94.1

OTHER PUBLICATIONS

Kreider et al. (2017) J. Intern. Soc. Sports Nutr. 14: 18 pages. (Year: 2017).*
Huihui Fu; Li Pan; Jingyun Wang; Jixing Zhao; Xin Guo; Jingya Chen; Shiling Lu; Juan Dong; Qingling Wang; Sensory Properties and Main Differential Metabolites Influencing the Taste Quality of Dry-Cured Beef during Processing. Foods 2022, 11, 531. https://doi.org/10.3390/foods11040531.
Ralf Jager; Martin Purpura; Andrew Shao; Toshitada Inoue; Richard B. Kreider. Analysis of the Efficacy, Safety, and Regulatory Status of Novel Forms of Creatine. Amino Acids (2011) 40:1369-1383. https://pubmed.ncbi.nlm.nih.gov/21424716/.
Roger J. Williams. Taste Deficiency for Creatine. Journal of the American Chemical Society 48: 536 (1926). https://www.science.org/doi/10.1126/science.74.1928.597.

* cited by examiner

*Primary Examiner* — Russell G Fiebig
(74) *Attorney, Agent, or Firm* — Richard Eldredge; Leavitt & Eldredge Law Firm

(57) ABSTRACT

Disclosed herein is disclosed is a nutritional food product (supplement) comprising creatine, which may be provided in a gummy form. In certain embodiments, the supplement may comprise about 6% to 35% by weight of creatine. In some embodiments, the supplement may comprise a gelling agent, a sweetener, and water.

20 Claims, 1 Drawing Sheet

CREATINE NUTRITIONAL SUPPLEMENT

RELATED APPLICATION

This application claims priority to U.S. application Ser. No. 17/221,787 filed Apr. 3, 2021, which claims benefit to Provisional Application No. 63/069,650, filed Aug. 24, 2020, all of which are incorporated by reference herein in their entirety.

BACKGROUND

The present disclosure relates generally to creatine nutritional supplements, including compositions, formulations, and combinations of ingredients in the creatine nutritional supplements, as well as processes for manufacturing embodiments of such supplements.

Creatine is believed to be associated with a number of benefits to the body. However, its relatively low-level of dissolvability and unpleasant taste makes creatine difficult to consume in water-soluble powder form. As such, an improved nutritional supplement and/or consumable item which incorporates creatine is desirable.

SUMMARY

According to various embodiments, disclosed is a nutritional food product (supplement) comprising creatine, which may be provided in a gummy form. In certain embodiments, the supplement may comprise about 6% to 35% by weight of creatine. In some embodiments, the supplement may comprise a gelling agent, a first sweetener comprising an oligosaccharide, a second sweetener comprising a disaccharide, a monosaccharide, or combination thereof saccharide(s), said second sweetener being present in an amount of at about 10% to 80% by weight, and water.

In certain embodiments, the food product may include creatine at about 6% to 35% by weight, pectin, a first sweetener comprising an oligosaccharide, a second sweetener comprising a disaccharide, a monosaccharide, or combinations thereof, said second sweetener being present in an amount of about at about 25% to 70% by weight, and water. In some embodiments, the disaccharide is by weight between about 30% and 60% or about 35% and 50%. In some embodiments, the creatine is by weight is between about 7% and 30%, about 8% and 25%, or about 12% and 13%. In some embodiments, the pectin is by weight between about 1% and 20%, or about 1.75% and 7%.

In some embodiments, the oligosaccharide is by weight between trace amounts and about 65%, about 25% and 55%, or about 30% and 50%. In some embodiments, the monosaccharide is by weight between 30% and 60% or about 35% and 50%. In some embodiments, the food product can include an acidifying agent and/or a buffer agent. The acidifying agent can be by weight between trace amounts and about 10%, or about 0.3% to 2.5%. The buffer agent can be by weight between trace amounts and about 3%, or about 0.2% and 1.5%. In some embodiments, the acidifying agent can be selected from the group consisting of lactic acid, formic acid, citric acid, malic acid, tartaric acid, and a combination thereof. The buffer agent can be selected from the group consisting of calcium citrate, sodium citrate, magnesium citrate, potassium citrate, zinc citrate, protein, amino acid, and a combination thereof. In some embodiments, the food product can include a natural flavor, the natural flavor can be a volatile substance such as ethanol.

In some embodiments, in the food product disclosed herein by weight percentages, the creatine can be between about 6% and 20%, the pectin can be between about 1.75% and 7%, the oligosaccharide can be between about 30% and 47.5%. the disaccharide can be between about 35% and 50%, and the water can be between about 5% and 16%. In some embodiments, in the food product disclosed herein by weight percentages, the creatine can be about 12.5%, the pectin can be between about 8% and 20%, the oligosaccharide can be between about 10% and 40%. the disaccharide can be between about 35% and 65%, and the water can be between about 2% and 5%.

In some embodiments of the food product disclosed herein, the oligosaccharide can be tapioca and the disaccharide can be cane sugar. The food product can include by weight sodium citrate between about 0.01% and 0.03%; citric acid between about 6% to 10%; malic acid between about 3% and 8%; a natural flavor between about 0.1% and 0.3%; spirulina between about 0.01% and 0.2%; organic blueberry between about 0.01% and 0.2.

In some embodiments, the food product can include creatine, gelatin, an oligosaccharide, a disaccharide at about 25% to 70% by weight, and water. In some embodiments, the creatine can be between about 5% to 20%, the gelatin can be between about 3% to 20%, and the water can be between about 5% to 20%.

Further disclosed herein is a method of producing the food product, which can include hydrating pectin with water under heat, solubilizing a disaccharide and an oligosaccharide, forming a mixture of the hydrated pectin and the solubilized disaccharide and oligosaccharide, adding a buffer agent to the mixture, adding creatine to the mixture, adding a natural flavor to the mixture, adding an acidifying agent to the mixture, cooking the mixture between about 85 to 115 Celsius for about 5 to 60 minutes, holding the mixture between about 90 to 100 Celsius for about 5 to 30 minutes, and depositing the mixture into a mold.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figures 1, 2:
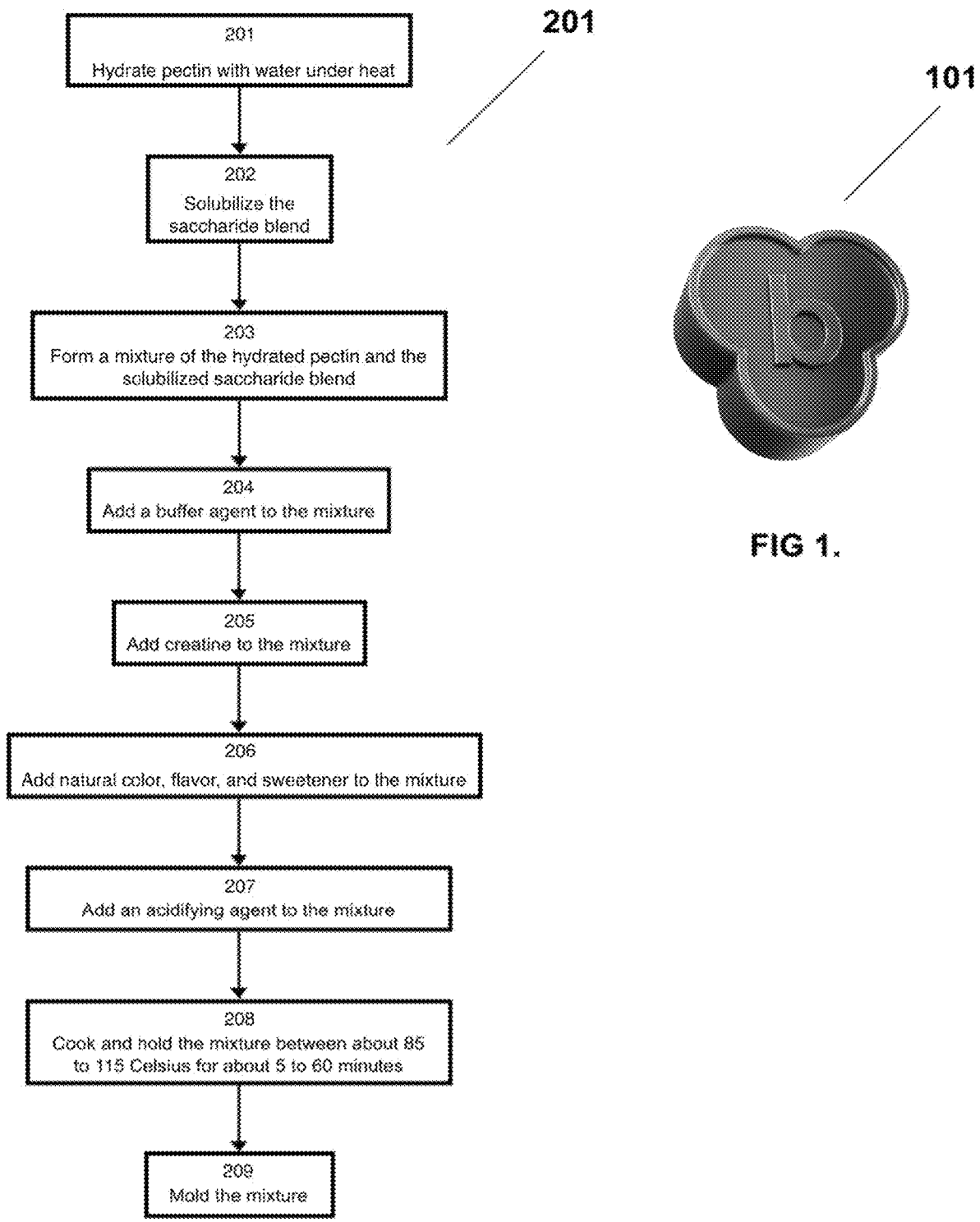
FIG. 1 depicts a gummy creatine nutritional supplement having a Venn diagram design, according to an exemplary embodiment.
FIG. 2 shows a flowchart illustrating a manufacturing process for the nutrition supplement, according to certain embodiments.

Creatine is believed to be one of the healthiest amino acids, which may be found in seafood and red meat. Creatine is also produced in the human body from the amino acids glycine and arginine, with an additional requirement for methionine to catalyze the transformation of guanidinoacetate to creatine. A non-limiting list of believed benefits of creatine include increasing strength, focus, short-term memory, and energy; assisting in muscle growth; boosting the immune system; fighting age-degenerative diseases; and slowing the signs of aging. However, the relatively low-level of dissolvability and unpleasant taste makes it difficult to consume in water-soluble powder form.

The disclosed subject matter provides an improved nutritional supplement (also referred to as "supplement" and "food product") that includes a specifically developed composition of ingredients in combination with creatine, that significantly reduces or eliminates the unpleasant creatine taste and insoluble characteristics.

In certain embodiments, the disclosed supplement may be formulated as a gummy or gelatin, which delivers all the benefits of the creatine contained therein. In different embodiments, the supplement may be formulated in other edible product forms. In certain embodiments, the supplement may further be infused with super foods and/or vitamins. In certain embodiments, the supplement may further include flavoring and/or sweeteners, agents which effectively mask the unpleasant taste of creatine and provide it with a pleasant and delicious tasting flavor making the supplement much more appealing to consumers. In various embodiments, this is effectively achieved without the use of excessive levels of sugar. In one embodiment, an amount of sugar is kept below a level which exceeds the solubility point, which can cause undesirable crystallization and hardening of the supplement. Moreover, excessive sugar can be undesirable for consumers with a goal of minimizing their daily sugar intake for health purposes. In further embodiments, coloring agent may be added to further enhance the supplements appeal. Additionally, the supplement may be provided in various fanciful forms/designs (such as the "Venn" diagram design depicted in FIG. 1) to enhance its appeal.

In some embodiments, the nutritional supplement disclosed herein may include creatine. In certain embodiments, the creatine may selected from the group comprising creatine monohydrate, creatine hydrochloride, creatine magnesium chelate, pH-buffered creatine, creatine citrate, creatine malate, di-creatine malate, liquid creatine, tri-creatine malate, creatine nitrate, creatine orotate, creatine phosphate, creatine gluconate, creatine pyruvate, creatine alphaketoglutarate, creatine ethyl ester, glycosylated creatine, effervescent creatine, micronized creatine, and combinations thereof. In one embodiment, the supplement may comprise creatine monohydrate, which may be sold under the brand name Creapure®. In certain embodiments, the concentration of creatine in the nutritional supplement in weight percentages may be from about 0.1% to about 50%, or from about 1% to about 45%, or from about 5% to about 40%, or from about 6% to about 35%, or from about 7% to about 30%, or from about 8% to about 25%, or from about 9% to about 20%, or from about 10% to about 15%, or from about 0.1% to about 30%, or from about 2.5% to about 25%, or from about 5% to about 20%. In some embodiments, the concentration of the creatine can be about 2.5% to 25% by weight. In some embodiments, the concentration of the creatine can be about 5% to 20% by weight. In some embodiments, the concentration of the creatine can be about 12% to 13% by weight. In some embodiments, the concentration of the creatine can be about 12.5% by weight.

In some embodiments, the nutritional supplement may comprise other amino acids ("secondary amino acids"), including but not limited to histidine, isoleucine, leucine, lysine, methionine, phenylalamine, threonine, tryptophan, valine, alanine, arginine, asparagine, aspartic acid, cysteine, glutamic acid, glutamine, glycine, ornithine, proline, selenocysteine, serine, tyrosine, L-Theanine, L-Tyrosine, and combinations thereof. In some embodiments, the nutritional supplement may comprise about 0.05% to about 10% of the secondary amino acid(s) by weight.

In certain embodiments, the nutritional supplement disclosed herein may include one or more sweeteners. In some embodiments, the sweetener may comprise a saccharide/polysaccharide. In certain embodiments, the sweetener may comprise an oligosaccharide. In some embodiments, the oligosaccharide can be a syrup. Exemplary syrups and/or oligosaccharides can include, but are not limited to, allulose syrup, glucose syrup, corn syrup, rice syrup, invert syrup, isomaltooligosaccharide (IMO) sugar, tapioca, fructooligosaccharide (FOS) syrup, starch, fiber syrup, inulin, fruit puree, fruit concentrate, high maltose syrup, agave syrup, and any combinations thereof. In some embodiments, the syrup can be a corn syrup including a dextrose equivalent (DE) of about 40 to about 70 DE. In some embodiments, the corn syrup comprises a DE of about 55 to 62 DE. In some embodiments, the corn syrup is about 62 DE. The corn syrup can be a high fructose corn syrup. In some embodiments, tapioca can be used. Some non-limiting concentrations of syrup in the nutritional supplement in weight percentages can include, but not limited to, about 0.1% to 80%, about 5% to 75%, about 10% to 70%, about 15% to 65%, about 20% to 60%, about 25% to 55%, about 30% to 50%, about 35% to 47.5%, about 1% to 65%, about 25% to 55% or about 30% to 47.5%. In some embodiments, the concentration of the syrup can be about 1% to 65% by weight. In some embodiments, the concentration of the syrup can be about 25% to 55% by weight. In some embodiments, the concentration of the syrup can be about 30 to 47.5% by weight.

In some embodiments, the sweetener may comprise non-organic cane sugar, organic cane sugar, sugar alcohol, natural sweeteners such as allulose, stevia or monk fruit, sugar alternatives such as short length carbohydrate, any of the plethora of artificial sweeteners known to one of ordinary skill in the art or which may become known, and any combinations thereof. In some embodiments, organic cane sugar can be used as a sweetener. In some embodiments, the sweetener may comprise a disaccharide. In certain embodiments, the disaccharide may comprise maltitol. In some embodiments, the sweetener may comprise a monosaccharide. In certain embodiments, the monosaccharide is present in an amount of at about 25% to about 70% by weight. In some embodiments, the monosaccharide is by weight between 30% and 60% or about 35% and 50%. In certain embodiments, the disclosed nutritional supplement may comprise a first sweetener comprising one or more oligosaccharide(s)/oligosaccharide syrup(s) ("oligosaccharide sweetener"), and a second sweetener comprising one or more sweeteners different from the oligosaccharide sweetener ("non oligosaccharide sweetener"). Some non-limiting examples of concentrations of the non-oligosaccharide sweetener in the nutritional supplement in weight percentages may be about 10% to about 80%, about 15% to about 75%, about 20% to about 70%, about 25% to about 65%, about 30% to about 60%, about 35% to about 55%, or about 40% to about 50%. In some embodiments, the concentration of the non-oligosaccharide sweetener can be about 25% to about 70% by weight. In some embodiments, the concentration of the non-oligosaccharide sweetener can be about 35% to about 60% by weight. In some embodiments, the concentration of the non-oligosaccharide sweetener can be about 42% to 50% by weight.

In some embodiments, the disclosed nutritional supplement may comprise a disaccharide and an oligosaccharide, with a weight ratio between the disaccharide and the oligosaccharide being about 0.2/1 to about 10/1, about 0.4/1 to about 9/1, about 0.6/1 to about 8/1, about 1/1 to about 6/1, or about 5/1. It shall be appreciated that any sweetener or combination of sweeteners may be used in alternate embodiments, and that the sweetener(s) may not necessarily comprise a disaccharide and/or an oligosaccharide in alternate embodiments.

In some embodiments, the nutritional supplement disclosed herein may include a gelling agent. Exemplary gelling agents can include, but not limited to pectin, gelatin, seaweed extract, agar, carrageenan, gum Arabic, and any combinations thereof. In some embodiments, pectin can be used as a gelling agent. In some embodiments, gelatin can be used as a gelling agent. Some non-limiting examples of concentrations of gelling agent in the nutritional supplement in weight percentages can be about 0.1% to about 60%, about 0.5% to about 50%, about 1% to about 40%, about 1.5% to about 35%, about 1.75% to about 30%, about 2% to about 20%, or about 5% to about 7%. In some embodiments, the concentration of the gelling agent can be about 1% to about 20% by weight. In some embodiments, the concentration of the gelling agent can be about 1.5% to about 10% by weight. In some embodiments, the concentration of the gelling agent can be about 1.75% to about 7% by weight. In some embodiments, the concentration of the gelling agent can be about 8% to about 20% by weight. In some embodiments, the concentration of the gelling agent can be about 1% to about 50% by weight. In some embodiments, the concentration of the gelling agent can be about 2% to about 30% by weight. In some embodiments, the concentration of the gelling agent can be about 3% to about 20% by weight.

In some embodiments, gelatin may be used as a gelling agent. Examples of gelatins can include but are not limited to 120 Bloom gelatin. 125 Blown gelatin, 160 Bloom gelatin, 190 Bloom gelatin. 200 Bloom gelatin, 220 Bloom gelatin. 250 Bloom gelatin, and any combinations thereof. The gelatin can be acid treated. In some embodiments, the gelatin has a bloom strength from about 80 to 250 Bloom, in some embodiments, the gelatin has a bloom strength from about 125 to 250 Bloom, in some embodiments, the gelatin has a bloom strength of about 160 to 250 Bloom. In some embodiments, the gelatin has a bloom strength of about 190 to 250 Bloom.

In some embodiments, the weight ratio between disaccharide and oligosaccharide in the disclosed nutritional supplement can be about 0.2/1 to 10/1, about 0.4/1 to 9/1, about 0.6/1 to 8/1, about 1/1 to 6/1, or about 5/1.

In some embodiments, the nutritional supplement disclosed herein can include water. Some non-limiting examples of water concentrations in the nutritional supplement in weight percentages can include about 0.1% to about 40%, about 0.5% to about 30%, about 1% to about 25%, about 2% to 20%, about 5% to 16%, about 7% to about 13%, or about 10% to about 12%. In some embodiments, the concentration of the water can be about 1% to about 25% based on the total weight of the nutritional supplement. In some embodiments, the concentration of the water can be about 2% to about 20% by weight. In some embodiments, the concentration of the water can be about 5% to about 16% by weight. In some embodiments, the concentration of the water can be about 2% to about 5% by weight. In some embodiments, the concentration of the water can be about 5% to about 20% by weight.

In some embodiments, the nutritional supplement disclosed herein may include an acidifying agent. Exemplary acidifying agents can include, but not limited to lactic acid, formic acid, citric acid, malic acid, fumaric acid, tartaric acid, glucono-delta lactone, salts of gluconic acid, phosphoric acid, succinic acid, adipic acid, ascorbic acid, acetic acid, and any combinations thereof, in some embodiments, citric acid can be used as an acidifying agent. Some non-limiting concentrations of the acidifying agents in the nutritional supplement in weight percentages may be from a trace amount to about 15%, about 0.1% to about 10%, about 0.2% to about 7%, about 0.3% to about 5%, about 0.5% to about 4%, about 0.7% to about 3%. or about 1% to about 2.5%. In some embodiments, the concentration of the acidifying agent can be from a trace amount to about 10% by weight. In some embodiments, the concentration of the acidifying agent can be about 0.2% to about 5% by weight. In some embodiments, the concentration of the acidifying agent can be about 0.3% to about 2.5% by weight.

In certain embodiments, the disclosed supplement may include an acidulant which may give a tart, sour, or acidic flavor to enhance the perceived sweetness of the supplement. The acidulant may further act as an acidifying agent. In certain embodiments, the acidulant may comprise citric acid, but is not limited to this option.

In some embodiments, the nutritional supplement disclosed herein may include a buffer/buffering agent. In certain embodiments, the buffer agent may comprise an acidifying agent. Exemplary acidifying agents can include, but not limited to sodium citrate, magnesium citrate, trisodium citrate, disodium citrate, calcium citrate, any protein or amino acids, and any combinations thereof. In some embodiments, sodium citrate can be used as a buffer agent. In some embodiments, sorbitol may be used as the buffering agent. Some non-limiting concentrations of the buffer agent in the nutritional supplement in weight percentages may be from trace amount to about 5%, about 0.1% to about 4%, about 0.2% to about 3%, about 0.3% to about 2%, about 0.4% to about 1%, or about 0.5% to about 0.7%. In some embodiments, the concentration of the buffer agent can be from trace amount to about 10% by weight. In some embodiments, the concentration of the buffer agent can be about 0.1% to about 2% by weight. In some embodiments, the concentration of the buffer agent can be about 0.2% to about 1.5% by weight.

In some embodiments, the nutritional supplement disclosed herein may include a flavorant. Exemplary flavorants may comprise oils including but not limited to lemon oil, spearmint oil, peppermint oil, cinnamon oil, oil of wintergreen (methylsalycylate), clove oil, bay oil, anise oil, eucalyptus oil, thyme oil, cedar leaf oil, oil of nutmeg, oil of sage, oil of bitter almonds, cassia oil, and any combinations thereof. The flavorants can include artificial, natural or synthetic fruit flavors such as citrus or fruit oils and/or essences including apple, apricot, banana, blueberry, cherry, grape, grapefruit, kiwi, lemon, lime, orange, pear, peach, pineapple, plum, raspberry, strawberry, tangerine and watermelon, or combinations thereof. In some embodiments, the concentrations of the flavorants in weight percentages can be from trace amount to about 0.6%, about 0.1% to about 0.5%, about 0.2% to about 0.4%, or about 0.15% to about 0.35%.

Other and/or additional flavorants may include, but are not limited to menthol, artificial vanilla, cinnamon derivatives, and various fruit flavors, individually or in admixture. Flavoring can also include, for example, aldehydes and esters including cinnamyl acetate, cinnamaldehyde, citral diethylacetal, dihydrocarvyl acetate, eugenyl formate, p-methylamisol, acetaldehyde (apple); benzaldehyde (cherry, almond), anisic aldehyde (licorice, anise); cinnamic aldehyde (cinnamon); citral, i.e., alpha citral (lemon, lime); ethyl vanillin (vanilla, cream); hellotropine, i.e., piperonal (vanilla, cream); vanillin (vanilla, cream); alpha-amyl cinnamaldehyde (spicy fruity flavors); butyraldehyde (butter, cheese); valcraldehyde (butter, cheese): citronellal; decannal (citrus fruits); CA 02864531 2014-09-19 aldehyde C-8 (citrus fruits); aldehyde C-9 (citrus fruits); aldehyde C-12 (citrus fruits); 2-ethylbutyraldehyde (berry fruits); tolyl aldehyde (cherry, almond); veratraldehyde (vanilla); 2,6-dimethyl-5-heptenal, i.e., melonal (melon); 2,6-dimethyloctanal (green fruit); and 2-dodecenal (citrus, mandarin), mixtures thereof and the like. Additional flavor compounds include ethylacetate, thiophene, ethylpropionate, ethyl bulyrate, and 2-hexanoate. 2-methylpyazine, heptaldehyde, 2-octanone, limonene, and eugenol.

In some embodiments, a natural flavor is used for the disclosed nutritional supplement food product. The natural flavor may include a volatile substance which can be easily evaporated at ambient pressure and temperature, in some embodiments, the volatile substance in the natural flavor may be an alcohol such as ethanol. It shall be appreciated that different types of flavor agents and combinations of different flavor agents may be used in alternate embodiments.

In some embodiments, the nutritional supplement disclosed herein may include a colorant. Exemplary colorants can include natural or uncertified colors from natural sources or certified colors for the effect of color. In some embodiments, the colorant can include dyes, certified aluminum lakes or colors derived from a natural source. The colorant may be water-based, oil-based or dry. The colorants may comprise primary colors, blends of colors or discrete mixtures of colors, such as confetti. The concentrations of the colorant in the nutritional supplement in weight percentages can be from trace amount to about 0.6%, about 0.1% to about 0.5%, about 0.2% to about 0.4%, or about 0.15% to about 0.35%.

In some embodiments, the nutritional supplement disclosed herein may include vitamins. Examples of vitamins can include, but are not limited to vitamin E, vitamin C, vitamin B2, vitamin B3, and vitamin B6, vitamin B9, and any combinations thereof. In certain embodiments, the nutritional supplement can include vitamin B9 from trace amount to about 0.10%, about 0.001% to about 0.05%, about 0.002% to about 0.01%, or about 0.003% to about 0.005% by weight. In some embodiments, the concentration of vitamin B9 may be about 0.003% by weight. According to an exemplary embodiment, a serving size which may comprise a gummy of approximately 4 grams may include B9 in about a trace amount to about 5,000 microgram (mcg), about 1 mcg to about 3.000 mcg, about 5 mcg to about 1,500 mcg, about 10 mcg to about 900 mcg, about 50 mcg to about 800 mcg, about 1 mcg to about 800 mcg, or about 50 mcg to about 1,000 mcg. In some embodiments, the nutritional supplement can include vitamin B12 from trace amount to about 0.10%, from about 0.00001% to about 0.05%, from about 0.00002% to about 0.01%, or form about 0.00003% to about 0.005% by weight. In some embodiments, the concentration of vitamin B12 may be about 0.00003% by weight. According to an exemplary embodiment, a gummy supplement of a serving size of about 4 g may comprise B12 in about a trace amount to about 100 mcg, about 0.1 mcg to about 50 mcg, about 0.12 mcg to about 38.4 mcg, about 0.24 mcg to about 19.2 mcg, about 0.6 mcg to about 9.6 mcg, about 0.12 mcg to about 9.6 mcg, or about 0.6 mcg to about 38.4 mcg. In certain embodiments, the vitamin B12 may comprise Cobalamin.

In some embodiments, the nutritional supplement can optionally comprise an emulsifier. Some non-limiting examples of emulsifiers may include sucrose esters, soy lecithin, sunflower lecithin, egg lecithin, lecithins and combinations thereof. In some embodiments, the nutritional supplement can include an emulsifier in weight percentages from trace amount to about 1%, about 0.2% to 0.8% trace amount to about 0.5%, about 0.5% to 1%, about 0.3% to 0.6%, or about 0.1% to 0.5%.

In some embodiments, the nutritional supplement of the present disclosure can optionally be coated with a wax and/or oil. Some non-limiting examples of suitable wax can include, but are not limited to carnauba wax, bees wax, and the like. Sone non-limiting examples of suitable oils can include, but are not limited to mineral oil, coconut oil vegetable oil, and the like. The nutritional supplement of the present disclosure can further be coated with a flavorant, such as sugar granules or flavor particles.

In further embodiments disclosed supplement may incorporate other active or non-active ingredients, including but not limited to herbal additives, ascorbic acid, cocoa powder (for a chocolate supplement), cocoa butter, palm kernel oil, sunflower lecithin, or soy lecithin. In some embodiments, the nutritional supplement may also include cannabidiol (CBD), ginger, tetrahydrocannabinol (THC), pepper, chili, cayenne, turmeric, collagen, butyric acid, salts or esters of beta-hydroxybutyric acid (BHB), or any combinations thereof. In some embodiments, the nutritional supplement can include spirulina, organic blueberry, or any combinations thereof.

FIG. 1 depicts an exemplary gummy design 101 for the creatine nutritional supplement, in accordance with an exemplary embodiment. It shall be appreciated that the disclosed supplement may be provided in various ingestible forms, which may be edible or non-edible, according to alternate embodiments. Such forms may include, but are not limited to chewable products, worms, caramel steering, hard candy, or chocolate. In some embodiments, the creatine nutritional supplement can include by weight about 10% to about 30% organic tapioca, about 2% to about 5% water, about 45% to about 65% organic cane sugar, about 12.5% creatine, about 8% to about 20% pectin, about 0.01% to about 0.03% sodium citrate, about 6% to about 10% citric acid, about 3% to about 8% malic acid, about 0.1 to about 0.3% natural flavor, about 0.01% to about 0.2% spirulina, about 0.01% to about 0.2% organic blueberry.

FIG. 2 depicts an exemplary process 201 for manufacturing the creatine nutritional supplements with a strongly mitigated or masked creatine tastes, according to certain embodiments. The process may comprise a step 202 of hydrating a gelling agent such as a pectin with water at an elevated temperature of about 90 to 100 Celsius and pH value of about 4.2 to 5.6. Process 201 may further comprise a step 203, of solubilizing a disaccharide and an oligosaccharide. In some embodiments, step 201 may be followed by step 203. In certain embodiments, process 201 may comprise a further step 204 of forming a mixture of the hydrated pectin and the solubilized disaccharide and oligosaccharide. In certain embodiments, process 201 may comprise a further step 205 of adding a buffer agent to the mixture formed in step 204 to maintain the mixture at a pH value of about 4.2 to 5.6. In some embodiments, this may be followed by a step 206 of adding creatine. In certain embodiments, process 201 may further comprise a step 207 of adding a natural flavor into the mixture. In certain embodiments, process 201 may further comprise a step 208 of adding an acidifying agent to the mixture. This may be carried out at an elevated temperature of about 80 to about 110 Celsius and a pH value of about 2.8 to about 3.7. In certain embodiments, process 201 may further comprise a step 209 of cooking the mixture which comprises holding the mixture at a temperature of between about 85 degrees Celsius to about 115 degrees Celsius for about 5 to about 60 minutes. The temperature range for cooking step 209 may vary with the specific gelling agent used, as known in the art. For example, if agar, gelatin, or starch is used, the temperature for step 209 in some embodiments may be between 30 and 90 degrees Celsius. As another example, if the gelling agent is carrageenan, the temperature for step 209 in some embodiments may be between 50 and 150 degrees Celsius. In certain embodiments, process 201 may further comprise a step 210 of depositing the mixture into a starch tray or silicone mold. Once this has been done, the mixtures may undergo drying. Finally, the mixture may be packaged for distribution.

It shall be appreciated that the pH levels may have varying ranges in alternate embodiments, depending on factors such as the specific type of gelling agent used. For example, if gelatin, pectin, or carrageenan are used, the pH in some embodiments may be kept between about 2 and about 6. If agar is used, the pH in some embodiments may be kept between about 3 and about 8. In some embodiments, if pectin is used, the pH in the finished product may be about 2.5 to about 4.

In some further embodiments, other properties and/or amount ranges may be varied to mask the flavor of the creatine. This may include, for example, adjusting the water activity (i.e., the ratio of the partial pressure of water in the atmosphere in equilibrium with the substrate (e.g., a food) to that of the atmosphere in equilibrium with pure water at the same temperature), adjusting brix (the sugar content of an aqueous solution), and adjusting the levels of acetic acid. In some embodiments, a water activity level may range between about 0.3 and about 0.85. In further embodiments, a brix value may range between about 0.65 and about 0.99. In further embodiment, acetic acid levels may range between about 1% and about 50%.

In some embodiments, the nutritional supplement in the present disclosure can have a density of from about 0.6 g/cubic centimeters (g/cc) to about 1.4 g/cc, about 0.7 g/cc to about 1.3 g/cc, about 0.8 g/cc to about 1.2 g/cc, about 0.9 g/cc to about 1.1 g/cc, about 0.8 g/cc to about 1.0 g/cc, about 1.0 g/cc to about 1.2 g/cc, about 0.9 g/cc to about 1.2 g/cc, about 0.7 g/cc to about 1.1 g/cc, about 0.85 g/cc to about 1.15 g/cc, about 0.95 g/cc to about 1.05 g/cc, or about 1.05 g/cc to about 1.25 g/cc.

The gel structure of the disclosed nutritional supplement product can be further characterized by textural analysis, such as firmness and resilience (also known as spring back). Firmness and resilience can be measured using a TA.TX texture analyzer (Texture Technologies; Hamilton, Mass.) using conventional methods. Firmness and resilience of the gel structure can be measured in grams force using a TA.TX texture analyzer in compression mode. In some embodiments, the nutritional supplement product can include a gel structure having a firmness measured in grams force of from about 450 g to about 1550 g, about 500 g to about 1400 g, about 700 g to about 1300 g, about 800 g to about 1200 g, about 900 g to about 1100 g, about 700 g to about 1000 g, about 850 g to about 1350 g, about 600 g to about 900 g, about 550 g to about 750 g, or about 925 g to about 1275 g.

In some embodiments, the nutritional supplement product can include a gel structure having a resilience of from about 20% to about 60% spring back after being held under about 20% compression strain for about one minute. In some embodiments, the nutritional supplement product can include a gel structure having a resilience of from about 25% to about 55% spring back, about 35% to about 45% spring back, about 30% to about 50% spring back, about 20% to about 40% spring back, about 40% to about 60% spring back, about 30% to about 60% spring back, or about 25% to about 45% spring back after being held under about 20% compression strain for about one minute. Over the shelf life of the nutritional supplement product, the spring back may be reduced by about 10% to about 80%, by about 20% to about 70%, by about 30% to about 60%, or by about 40% to about 50%.

In some embodiments, firmness and/or resilience can be measured at one or more time points during the shelf-life of the nutritional supplement product. In some embodiments, the firmness and/or resilience can be measured at about 0 days to 90 days after production of the nutritional supplement product; at about 1 day to 100 days after production of the nutritional supplement product; or at about 7 days to 80 days after production.

The nutritional supplement product of the present disclosure can be provided in multiple sizes and shapes as desired, including but not limited to, geometric shapes such as a cylinder, sphere, cube, pyramid, and the like; and novelty shapes such as novelty characters, bears, stars, worms, rings fruit, and the like. In some embodiments, the nutritional supplement product can be in the shape of a substantially rounded cylinder, such as a dot form or rounded, truncated cone, or cylinder form. The individual pieces in that embodiment can have a diameter of from about 14 mm to 18 mm, about 12 mm to 20 mm, about 13 mm to 15 mm, or about 15 mm to 18 mm. The individual pieces in that embodiment can have a height of from about 14 mm to 22 mm, about 15 mm to 20 mm, about 16 mm to 18 mm or about 17 mm to 22 mm. In some embodiments, the weight of an individual piece can be from about 1 gram to about 10 grams, about 1 gram to about 8 grams, about 1 gram to about 6 grams, about 1 gram to about 4 grams, about 2 grams to about 4 grams, about 2.2 grams to about 2.8 grams, about 2.5 grams to about 3.5 grams, or about 3 grams to about 4 grams. In some embodiments, the weight of an individual piece can be about 4 grams.

EXAMPLE

According to an exemplary embodiment, the disclosed supplement provided in a gummy form may comprise the following ingredients: about 0.25 grams of pectin; about 2.41 grams of water; disaccharide comprising about 0.88 grams of maltitol; a buffering agent comprising about 0.88 grams of sorbitol; an oligosaccharide comprising about 2.41 grams of inulin syrup; about 0.1 grams of citric acid; about 0.1 grams of malic acid; about 0.014 grams of Stevia extract; about 0.025 grams of McFona® Blueberry Flavor; about 0.071 grams of natural and artificial colors; about 1 gram of Creapure® creatine monohydrate; other amino acids including about 0.017 grams of L-Theanine, and about 0.017 grams of L-Tyrosine; about 0.00014 grams of Cobalamin (Vitamin B12); and about 0.000016 grams of Huperzine A.

It shall be appreciated that the disclosed supplement and process can have multiple configurations in different embodiments. It shall be appreciated that the supplement and process described herein may comprise any alternative known ingredients in the field and be of any size and/or dimensions. It shall be appreciated that the supplement may be produced using any known techniques in the field, and that the order and parameters of the process steps listed herein may be varied in alternate embodiments.

As used herein, the articles "a" and "an" are intended to include one or more items and may be used interchangeably with "one or more." Where only one item is intended, the term "one" or similar language is used. Also, as used herein, the terms "has", "have", "having", "with" or the like are intended to be open-ended terms. Further, the phrase "based on" is intended to mean "based, at least in part, on" unless explicitly stated otherwise.

The constituent elements of the disclosed supplement and process listed herein are intended to be exemplary only, and it is not intended that this list be used to limit the scope of the disclosure to just these elements. Persons having ordinary skill in the art relevant to the present disclosure may understand there to be equivalent ingredients and/or process steps that may be substituted within the present disclosure without changing the essential characteristic of the disclosed subject matter. Any discussion of numerical values or ranges such as weight percentages and pH values can be understood as referring to the exact values or reasonable approximations of those values/ranges as would be understood to a person of ordinary skill in the art. Terms such as 'approximate,' 'approximately,' 'about,' etc., as used herein indicate a deviation of within +/−10%. Relationships between the various elements of the disclosed device as described herein are presented as illustrative examples only, and not intended to limit the scope or nature of the relationships between the various elements. Persons of ordinary skill in the art may appreciate that numerous configurations may be possible to enjoy the functional benefits of the inventive subject matter. Thus, given the wide variety of configurations and arrangements of embodiments of the present disclosure the scope of the invention is reflected by the breadth of the claims below rather than narrowed by the embodiments described above.

What is claimed is:

1. A food product comprising:
    creatine at about 6% to 35% by weight based on total weight of the food product;
    a gelling agent; and
    at least one sweetener present in an about of about 10% to about 90% by weight based on total weight of the food product; and
    water,
    wherein the food product is a gummy;
    wherein the gelling agent is hydrated with water at an elevated temperature of about 90 to 100 degree Celsius and a pH balance of 4.2 to 5.6;
    wherein a mixture is formed between the at least one sweetener and the gelling agent;
    wherein the creatine is added to the mixture to create a finished product having a pH balance of 2.5 to 4.

2. The food product of claim 1, wherein the sweetener comprises an oligosaccharide.

3. The food product of claim 2, wherein the oligosaccharide is present in an amount of between trace amounts and about 65%, based on total weight of the food product.

4. The food product of claim 3, wherein the oligosaccharide is present in an amount of between about 25% and about 55% by weight, based on total weight of the food product.

5. The food product of claim 2, wherein the oligosaccharide is selected from the group comprising glucose syrup, corn syrup, rice syrup, invert syrup, isomaltooligosaccharide (IMO) sugar, tapioca syrup, fructooligsaccharide (FOS) syrup, starch, fiber syrup, inulin, fruit puree, fruit concentrate, high maltose syrup, agave syrup, and combinations thereof.

6. The food product of claim 2, wherein the sweetener further comprises a disaccharide, a monosaccharide, or combination thereof.

7. The food product of claim 6, wherein the disaccharide is present in an amount of between about 10% and about 50% by weight, based on the total weight of the food product.

8. The food product of claim 1, wherein the sweetener is present in an amount of at least 80% by weight based on total weight of the food product.

9. The food product of claim 1, wherein the sweetener selected from the group comprising allulose, beet sugar, cane sugar, erythritol, isomalt, lactitol, maltitol, maltose, mannitol, sucrose, xylitol, or combination thereof.

10. The food product of claim 1, further comprising a buffer agent.

11. The food product of claim 1, further comprising an acidulant.

12. The food product of claim 1, further comprising a coloring agent.

13. The food product of claim 1, further comprising a flavoring agent.

14. The food product of claim 1, wherein the creatine is selected from the group comprising creatine monohydrate, creatine hydrochloride, creatine magnesium chelate, pH-buffered creatine, creatine citrate, creatine malate, di-creatine malate, liquid creatine, tri-creatine malate, creatine nitrate, creatine orotate, creatine phosphate, creatine gluconate, creatine pyruvate, creatine alphaketoglutarate, creatine ethyl ester, glycosylated creatine, effervescent creatine, micronized creatine and combinations thereof.

15. The food product of claim 1, wherein the gelling agent is pectin.

16. The food product of claim 1, wherein the creatine is present in an amount of between about 7% and about 30% by weight, based on total weight of the food product.

17. The food product of claim 1, wherein the creatine is present in an amount of between about 8% to about 25% by weight, based on total weight of the food product.

18. The food product of claim 1, wherein the creatine is present in an amount of between 12% and about 13% by weight, based on total weight of the food product.

19. The food product of claim 1, wherein the gelling agent is present in an amount of between about 1% and about 20% by weight, based on total weight of the food product.

20. The food product of claim 1, wherein the gelling agent is present in an amount of between 1.75% and 7% by weight, based on total weight of the food product.

* * * * *